US00PP16651P3

(12) United States Plant Patent

Foley, Jr.

(10) Patent No.: US PP16,651 P3
(45) Date of Patent: Jun. 13, 2006

(54) **PLANT VARIETY OF *VINCA MINOR* NAMED 'GIANT STEPS'**

(50) Latin Name: *Vinca minor*
Varietal Denomination: Giant Steps

(75) Inventor: Thomas M. Foley, Jr., Woodland, CA (US)

(73) Assignee: Hines Nurseries, Inc., Irvine, CA (US)

( * ) Notice: Subject to any disclaimer, the term of this patent is extended or adjusted under 35 U.S.C. 154(b) by 95 days.

(21) Appl. No.: 10/882,781

(22) Filed: Jun. 30, 2004

(65) Prior Publication Data

US 2006/0005289 P1 Jan. 5, 2006

(51) Int. Cl.
*A01H 5/00* (2006.01)

(52) U.S. Cl. ..... Plt./226

(58) Field of Classification Search ..... Plt./226
See application file for complete search history.

*Primary Examiner*—Anne Marie Grunberg
*Assistant Examiner*—Annette H Para
(74) *Attorney, Agent, or Firm*—Christie, Parker & Hale, LLP

(57) ABSTRACT

A new plant variety of *Vinca minor* with larger leaf size and significantly heavier leaf substance.

2 Drawing Sheets

Botanical classification: *Vinca minor* (L.) 'Giant Steps'.

BACKGROUND OF THE INVENTION

The present invention relates to a new and distinct variety of *Vinca minor* which was discovered as a branch sport in a controlled planting of *Vinca minor* 'Bowles' (not patented) in Vacaville, Calif., by the originator Thomas M. Foley, Jr. The varietal denomination of the new variety is 'Giant Steps'.

The genus *Vinca* is included in the family Apocynaceae, which comprises about 130 genera and 2,100 species of worldwide distribution, generally scandent herbaceous perennials, shrubs and trees. The genus *Vinca* comprises approximately 12 species of groundcovers originating in Europe and Asia Minor, many of which possess desirable ornamental characteristics.

*Vinca minor* is widespread and common throughout much of Europe and Asia Minor. It generally has oval to elliptic leaves, 2 to 4 cms long, tapered to the base. Flowers are lilac blue, 2 cms wide, blooming from spring to early fall. Leaf color ranges from green to various forms of variegation, depending on the selected cultivar, light intensity and cultural conditions.

SUMMARY OF THE INVENTION

The new variety was discovered as a branch sport in a controlled planting of *Vinca minor* 'Bowles' and differs from its parent by larger leaf size, and significantly heavier leaf substance. *Vinca* m. 'Giant Steps' was asexually reproduced in Vacaville, Calif. Asexual reproduction of the new variety by stem cuttings, have confirmed that the distinctive characteristics of the new variety are stable and transmitted to succeeding generations, and the new variety reproduces true to type.

COMPARISON WITH PARENT

'Giant Steps' is distinguished from its parent and all other varieties of *Vinca minor* of which I am aware by larger leaf size, and significantly heavier leaf substance.

BRIEF DESCRIPTION OF ILLUSTRATIONS

The accompanying illustrations show a specimen of the new cultivar in a photo illustration as true to color as is reasonably possible to make in an illustration of this character.

DETAILED DESCRIPTION OF THE NEW VARIETY

Figure 1:
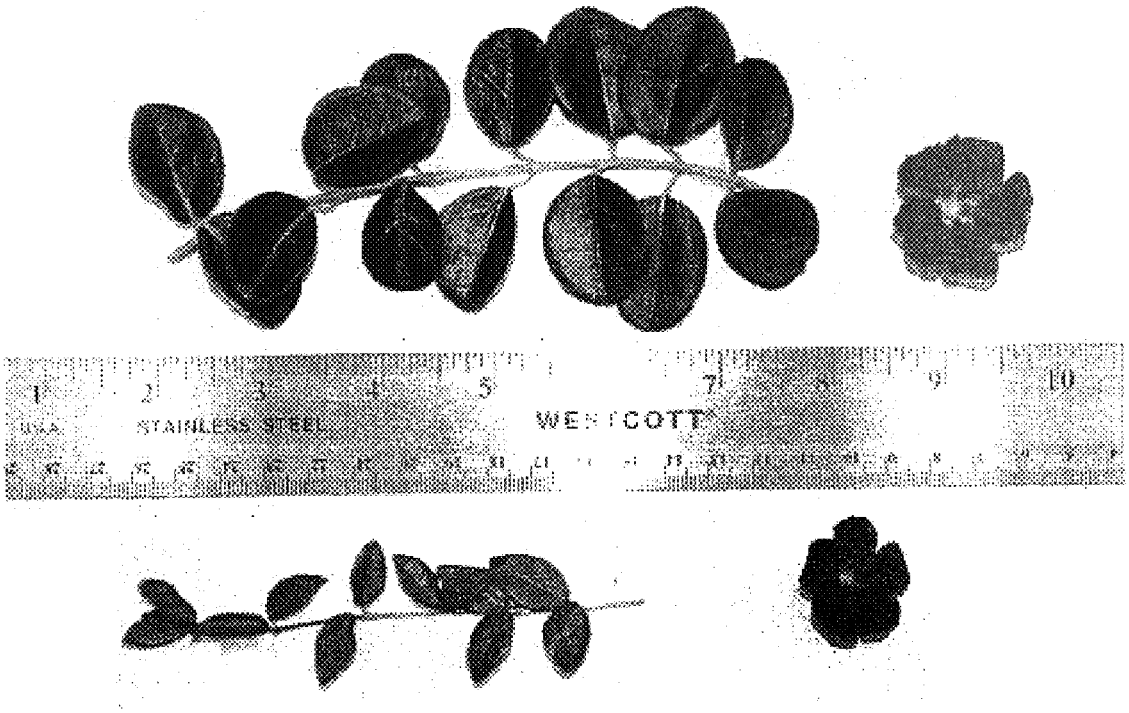
FIG. 1 illustrates the new variety (on top) and the parent *Vinca minor* 'Bowles' (bottom) with both foliage and flower.
Figure 2:
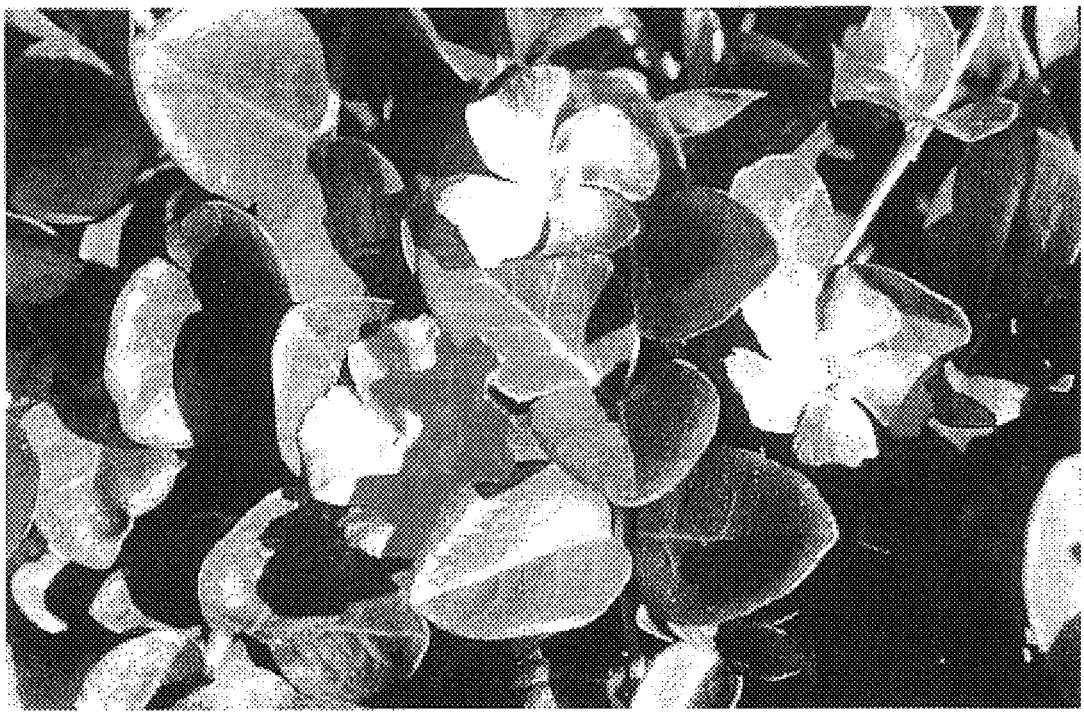
FIG. 2 illustrates the overall habit of the new variety.

'Giant Steps' has not been observed under all possible environmental, cultural and light conditions. The following observations and descriptions are of 1-year-old plants grown in Vacaville, Calif. in full sun, in a production nursery setting, in one-gallon nursery containers. In this description, color references are to The Royal Horticultural Society Colour Chart (2002) and terminology used in the color descriptions herein refers to plate numbers in this color chart. Phenotypic expression may vary with light intensity, cultural and environmental conditions.

Classification:

*Botanical.*—*Vinca minor* (L.) 'Giant Steps'.

*Parentage.*—Branch sport from *Vinca minor* 'Bowles' (not patented).

*Propagation.*—Stem cuttings (leaf and node).

Plant:

*Size.*—Approximately 10 cms tall (average) and up to approximately 3 meters in length.

*Habit.*—Prostrate, creeping. Stems arise vertically from the crown and may stay erect and reach a height of 15–20 cm but they typically elongate into a vine of indeterminate length. The vine stems become prostrate as they elongate and form infrequent branches.

*Branching.*—Suffrutiscent (woody at the base and more herbaceous terminally). Lateral Branches: More than 30. Typical # Branches: More than 30. Observed # Branches: 18. Diameter: 3 mm. Color: Green Group near 138B. Color of New Shoots: Near Green Group 138B. Color of Mature Shoots: Near Green Group 138B.

Leaf:

*Shape.*—Mostly orbicular to ovate.

*Leaf size.*—Up to 4 cms long; up to 3.5 cms wide.

*Arrangement.*—Opposite.

*Margin.*—Entire, cupped on underside.

*Texture/substance.*—Glabrous.

*Color.*—Young Foliage: Upper side: Near Green Group 137B. Under side: Near Green Group 138D. Mature Foliage Upper side: Near Green Group 137A. Under side: Near Green Group 138A–B.

*Venation.*—Pattern: Upper Surface: Not prominent. Under Surface: Not prominent.

*Petioles.*—Curved so that the opposite leaves are on the same plane and held above the stem. Size: Approximately 1 cm. Coloration: Near Green Group 138B. Texture: Glabrous. Internodes: Up to 2 cms long.

*Hardiness.*—USDA Zone 4 (−30° F. to −20° F.).

*Vigor.*—Rapid growth habit.

*Pests/diseases.*—None noted.

Inflorescence:

*Bloom period outdoors.*—Blooms in early-mid spring and sporadically later in the season.

*Greenhouse.*—Not grown in a greenhouse setting.

*Flower form.*—Salverform.

*Flower arrangement.*—Solitary.

*Flower size.*—Approximately 2.0 to 2.7 cms diameter; approximately 2 cm deep.

*Fragrance.*—None noted.

*Lastingness of individual blooms.*—Up to one month.

*Sepals.*—Number: 5. Shape: Apices: Acute. Size: Approximately 5 mm long, approximately 2 mm wide. Margin: Entire. Color: Green Group near 143C–D.

*Corolla.*—Near Violet — Blue Group near 93B, 5-petalled, sympetalous, irregular, non-overlapping. Lobes are 1.1–1.2 cm in length, 0.4 cm to 1.1 cm at tip in width, orifice 5 mm. Orifice color is near Violet — Blue Group near 91D.

Reproductive organs:

*Androecium.*—Stamens: Pentandrous, included, adnate to corolla. Filament Color: Near Yellow Green Group 145 B–C. Pollen Color: Near Yellow Group 11 C–D.

*Gynoecium.*—Pistil Single, included. Length: Approximately 7 mm. Stigma Color: Near White Group 155 A–C. Style Color: Near Yellow Green Group 145 C–D. Ovary Color: Near Yellow-Green Group 144 B–C. Fruit Not observed. The small, cylindrical fruit follices of *Vinca minor* are very rarely ever observed in cultivation.

I claim:

1. A new and distinct *Vinca minor* plant of the variety substantially as shown and described herein.

* * * * *